United States Patent [19]

Cruz, Jr.

[11] Patent Number: 4,578,067
[45] Date of Patent: Mar. 25, 1986

[54] HEMOSTATIC-ADHESIVE, COLLAGEN DRESSING FOR SEVERED BIOLOGICAL SURFACES

[75] Inventor: Mamerto M. Cruz, Jr., Pennington, N.J.

[73] Assignee: Alcon (Puerto Rico) Inc., Humacao, Puerto Rico

[21] Appl. No.: 708,008

[22] Filed: Mar. 4, 1985

Related U.S. Application Data

[63] Continuation of Ser. No. 367,455, Apr. 12, 1982, abandoned.

[51] Int. Cl.$^4$ .................. A61L 15/00; A61F 13/16
[52] U.S. Cl. .................. 604/368; 128/156; 128/DIG. 8
[58] Field of Search .............. 604/380, 368; 128/156, 128/DIG. 8

[56] References Cited

U.S. PATENT DOCUMENTS

| | | | |
|---|---|---|---|
| 2,451,915 | 10/1948 | Buresh | 19/89 |
| 3,046,986 | 7/1962 | Harwood | 604/380 |
| 3,534,454 | 10/1970 | Okamura | 28/72.2 |
| 3,742,955 | 7/1973 | Battista et al. | 128/334 R |
| 3,810,473 | 5/1974 | Cruz et al. | 128/334 |
| 4,016,877 | 4/1977 | Cruz et al. | 128/156 |
| 4,044,768 | 8/1977 | Mesek et al. | 128/287 |
| 4,148,664 | 4/1979 | Cruz | 106/161 |

OTHER PUBLICATIONS

Rando Web Process Pamphlet, Rando Machine Corp. (1976).

Primary Examiner—C. Fred Rosenbaum
Assistant Examiner—Sherri E. Vinyard
Attorney, Agent, or Firm—James A. Arno; Gregg C. Brown

[57] ABSTRACT

Hemostatic-adhesive, collagen dressings in the form of dry-laid, non-woven, self-supporting webs of collagen fibers and methods for preparing those webs are disclosed. The webs are formed from a mass of hemostatic-adhesive, collagen fibers having a moisture content of from about 7% to about 15% by weight, and retain the hemostatic-adhesive properties of the mass of collagen fibers.

19 Claims, No Drawings

HEMOSTATIC-ADHESIVE, COLLAGEN DRESSING FOR SEVERED BIOLOGICAL SURFACES

This application is a continuation of application Ser. No. 367,455, filed Apr. 12, 1982, now abandoned.

This invention relates to a method of forming dry-laid non-woven self-supporting sheets or webs consisting essentially of fine fibers derived from collagen which are particularly suited for medical and surgical purposes.

It has been known that collagen in various treated and prepared forms is useful in medical and surgical procedures and in the treatment of wounds. Collagen in certain forms has hemostatic properties when used as a wound dressing and has a low level of antigenicity. In the U.S. Patent to Orlando A. Battista, Mamerto M. Cruz, Jr., and Merritt R. Hait, U.S. Pat. No. 3,742,955 granted July 3, 1973, there is described a fluffy mass of a fine fibrous collagen product derived from natural collagen which when wet with blood has hemostatic properties and a unique self-adhesive property which is sufficient to join together severed biological surfaces. This bulk form of fine fibers demonstrates an unexpected and entirely unique self-adhesive property when wet with blood in live warm blooded animals and adheres to severed tissues without the use of sutures.

As described in the aforementioned patent, the hemostat-adhesive material is in the form of a fluffy mass of fine fibers and the fibers for use in the present invention consist essentially of a water-insoluble, ionizable, partial salt of collagen, the fibrous mass having a density of not more than about 8 pounds per cubic foot (0.128 gm./cc.), preferably the bulk density is between 1.5 and 6.0 pounds per cubic foot (0.024 and 0.096 gm./cc.) The fluffy or bulky mass when combined with blood in a wound forms a mass or plug that is self-adherent to the tissue surfaces and will seal the wound without the use of sutures. The partial salt of collagen consists essentially of an ionizable, water-insoluble, partial acid salt of collagen containing from about 50% to about 90% of the theoretical stoichiometric amount of the ionizable acid. The fluffy mass of fine fibers for use in the present invention may be prepared as described in the aforementioned patent.

Because of the low density and fluffiness of the product of the aforementioned patent, it is necessary to transfer the product to the wound by the use of forceps or manually with rubber gloves. In such handling procedures fibers become dislodged from the bulk being handled and portions will adhere to the forceps or rubber gloves. Although the fluffy fibrous mass is highly efficacious as a hemostat-adhesive material, the bulkiness and structureless nature of the product is a decided disadvantage from a handling standpoint and from the standpoint of delivering the product to a wound site.

Because of the sensitivity to water of the fine fibers of the partial salts of collagen having the hemostatic and unique adhesive characteristics as described in the aforementioned patent, fibrous sheets or webs formed from such fibers slurried in water are harsh and boardy and film-like in structure. When the fibers are wetted with water, the fibers swell. As the swollen fibrous mass dries, the fibers coalesce of bond together to form a film-like surface with a loss of the fibrous structure. The loss of fibrous structure results in a corresponding loss of hemostatic, adhesive, and delamination efficacy.

In the U.S. Patent to Mamerto M. Cruz, Jr., Orlando A. Battista, LaVerne C. Tressler and Carmine Cirolla, U.S. Pat. No. 3,810,473 granted May 14, 1974, there is disclosed a liquid-laid, non-woven, fibrous web having hemostatic and adhesive properties formed from this fluffy mass of finely-fiberized fibers. As disclosed in this patent, the production of products having a harsh structure is avoided by slurrying the hemostat-adhesive fibers in a liquid consisting of a mixture having a composition, by volume, in the range of from 95% organic liquid and 5% water to about 85% organic liquid and 15% water.

In the U.S. Patent to Mamerto M. Cruz, Jr., John M. Tenery and LaVerne C. Tressler, U.S. Pat. No. 4,016,877, granted Apr. 12, 1977, there is disclosed a method of forming a liquid-laid, non-woven, fibrous web by slurrying the fibers in 100% ethanol containa small proportion of concentrated hydrochloric acid, depositing the fibers to form a sheet or web, pressing the sheet under a limited pressure followed by freeze drying the sheet or web. The only water contained in the slurrying liquid is that which is introduced by adding the hydrochloric acid, that which may be absorbed from the ambient atmosphere and that which is contained in the fibers. This added water amounts to from about 1.03% to about 5%.

These methods requiring the use of ethanol are disadvantageous because of the cost of the ethanol, about 3 liters of ethanol being required to produce a 6 inch by 6 inch (12.25 × 12.25 cm.) final trimmed sheet. Also, the open handling of large volumes of 100% ethanol presents certain hazardous conditions. Probably a further disadvantage in the use of ethanol is the possibility of the product absorbing ethanol soluble contaminants originating from the processing equipment.

Reference has been made to the use of ethanol for the preparation of the liquid-laid webs. The ethanol may be replaced by other low molecular weight alcohols, ketones and the like such as, for example, methanol, isopropanol, amyl alcohol, methylethyl ketone, acetone, and mixtures of these organic liquids. The use of the organic liquids other than ethanol is feasible. However, for surgical uses it is essential that the product be completely freed of such solvents which is difficult, if not impossible. The handling of the large volumes of these solvents also presents hazardous conditions and the possibility of contamination.

The present invention provides a means of producing non-woven, self-supporting sheets or webs which retain the hemostatic-adhesive properties of the mass of fibrous partial salt of collagen. The invention also overcomes the disadvantages of the use of volatile solvent slurrying liquids.

The present invention also provides a method of forming dry-laid, non-woven self-supporting sheets or webs of the fluffy, fibrous collagen derived product which are flexible, non-flaking and possess sufficient cohesiveness to withstand normal handling in use and in shipping without separation of individual fibers.

The present invention provides dry air-laid, non-woven, self-supporting webs which retain the hemostatic-adhesive properties of the constituent fluffy, fibrous, partial salt of collagen.

Advantages of this invention will become apparent to those skilled in the art from the following description of the method and product.

In accordance with this invention, dry, air-laid, non-woven, self-supporting webs are formed from fine fibers of ionizable, water-insoluble, partial salts of collagen by an air laying technique. The webs may be produced by the use of conventional web forming equipment. Conveniently, the webs may be produced by supplying the fibers to a conventional 12 inch integrated Rando-feeder and Rando-webber. The Rando-feeder opens the mass of fibers and delivers the opened fibers to the Rando-webber. The Rando-webber converts the fibers into a randomly air-laid or unoriented bulky web. The web is calendered so as to improve the integrity of the web while retaining the absorbent and hemostatic-adhesive properties.

The fluffy mass of fibers of the ionizable, water-insoluble, partial acid salts of collagen may be formed by any method, preferably they are produced in accordance with the method disclosed in the patent to Mamerto M. Cruz, Jr., U.S. Pat. No. 4,148,664 granted Apr. 10, 1979. In producing the fibers, hydrochloric acid is preferred because it is relatively inexpensive, allows ready flexibility and ease of control. Other ionizable acids are satisfactory, such as, for example, hydrobromic acid, phosphoric acid and sulfuric acid. Sulfuric acid, for example, is satisfactory, but control of the action on the collagen is difficult. "Ease of control" has reference to the ability to arrest the swelling and hydrolysis of the collagen fibers so as to prevent the rapid degradation of the collagen to a water-soluble product. The partial acid salts contain from about 50% to about 90%, preferably between about 60% and 85%, of the theoretical stoichiometric bound acid content.

As compared to the usual spun collagen fibers and conventional textile fibers having smooth surfaces and which may be readily converted into non-woven webs by the use of the Rando equipment, the fibers of the ionizable, partial salts of collagen are very weak. Accordingly, in order to partially overcome the low strength and avoid fragmentation of the fibers utilized in producing the webs of this invention, it is essential that the fibers contain at least about 7%, by weight, moisture. This minimum moisture content is critical so as to plasticize the fibers. Further such minimum moisture content is critical to minimize electrostatic charge effects on the fibers. Also, in the passage of the dispersed fibers which are accompanied by some short fibers that unavoidably become fragmentized from the fibers and fiber bundles, the aforementioned minimum moisture content must be maintained so as to avoid the possibility of "dust explosions." Further, when the mass of fibers develop electrostatic charges, a substantial proportion of the fibers will deposit on the sides of the equipment. These fibers that are carried by the air stream and are deposited on the collector screen will not be completely randomized. The resulting sheet or web is non-uniform in thickness because the fibers have not been distributed uniformly across the screen and thereby produce thick and thin areas.

The fibers from the Rando-feeder are introduced into the air stream of the Rando-webber by the lickerin drum which combs the fiber bundles from a feed mat. The lickerin drum in effect introduces the fibers into the air stream as a homogeneously dispersed mass. The action of the lickerin drum is comparable to the action of a carding machine for ordinary textile fibers. Under optimized air flow conditions the fiber mass of uniform density is deposited across the collector screen as the air passes through the screen into the collector drum. Under these conditions, such web is exceedingly weak. Calendering of the web under proper moisture conditions must be relied upon to impart required web strength.

The moisture content of the fibers should not exceed about 15% due to the high sensitivity of the fibers to moisture. When the moisture content exceeds about 15%, clumping of the fibers occurs in the air stream and, accordingly, a sheet is formed having thick and thin areas, thick areas being created where clumps of fibers deposit. Also, when the moisture content of the fibers is too high, the fibers adhere to the collector screen and a non-uniform or even a discontinuous fibrous sheet is separated from the screen. Following collection of the laid sheet or web which is exceedingly weak, the web must be pressed and/or calendered. If the moisture content exceeds about 15%, an excessive bonding of the fibers occurs and the web may approach a somewhat boardy state or condition. A boardy state of the sheet drastically reduces the hemostatic efficacy. With excessive moisture content, the fibers and fiber bundles coalesce. This action creates a condition which might be likened to hornification and results in a decrease in the liquid absorbency and hemostatic efficacy of the web structures. Thus, in order to maintain the hemostatic efficacy of the fibers and other desired properties it is critical that the moisture content of the mass of fibers be within the range of about 7 to about 15% by weight, preferably between 8 and 11%.

The formation into a continuous random fiber web structure of this invention is similar to air-laid webs of natural and synthetic polymeric fibers. The coherency of such webs or web strength development is provided by further processing. For synthetic thermoplastic fibers, the web is heated sufficiently to soften the fiber and effect weld-like bonds at fiber crossings by pressing or embossing. Alternatively, the bulk web may be subjected to mechanical needling which causes an entanglement of fibers followed by calendering. For natural fibers in web form, the web may be impregnated with a suitable binder, or the web may be needled.

Because of the mechanical treatment to which the fibers are subjected in the Rando equipment, particularly by the lickerin drum, it is essential that the moisture content of the fibers be within the aforesaid range. If the moisture content is too low, many of the fibers are fragmentized which adversely affects the hemostatic efficacy of the sheet or web that is formed. Further, electrostatic charges build up with attendant difficulties described above such as shortening fibers, poor sheet or web formation, etc. If the moisture content is too high, clumping of the fibers occurs and a non-uniform sheet or web is formed on the collector screen. Subsequently, during calendering of webs having thick and thin areas, dense parchment-like structures are formed at the thick areas; that is, at the locations of fiber clumps creating the thick areas.

With air as the fiber conveying medium, it is essential that the circulating air contain sufficient moisture to avoid drying out the fibers. The ambient atmosphere and the circulating air in the equipment should be preferably maintained at a temperature of 70° to 75° F. (21° to 24° C.) and an RH of about 50 to 55%. Such conditions during the operation will result in the production of a sheet or web having a moisture content of approximately the same as that of the fibers introduced into the Rando-feeder.

The unsupported web as delivered by the Rando-webber is exceedingly weak and in order to provide the required coherency and integrity it is calendered with plain or embossing rolls. The moisture content of the sheet is very critical at this stage of web formation. The moisture functions as a plasticizer and during calendering also functions as a bonding agent which is a unique agent for the production of the coherent fibrous web structures. If the moisture content is below about 5% at this stage, poor inter-fiber bonding can occur. Although this magnitude of moisture when calendering with the use of embossing rolls is satisfactory, when using plain rolls the moisture content should be at least about 7%. Preferably, the moisture content during calendering should not exceed about 12%. During calendering of webs having moisture contents within these limits, a sufficient bonding between the fibers is effected to provide the required coherency and integrity of the sheet or web without an adverse affect upon the hemostatic properties. These conditions result in the formation of highly efficacious hemostatic-adhesive webs.

One of the advantages of producing the webs in accordance with the present invention is the ability to reprocess the fibers through the Rando equipment providing the web formed has not been calendered. In the event of the malfunctioning of the Rando-webber whereby the web does not meet specifications as to thickness, uniformity, weight per unit area, such defective web may be withdrawn prior to calendering. Similarly, if the moisture content of the web is not satisfactory for calendering, the web may be withdrawn prior to calendering. Such withdrawn web may be supplied to the Rando-feeder to reopen the mass into fibers which are then delivered to the Rando-webber. On the other hand, when producing webs by a liquid-laid method as described above, once a web is formed the web can not be reprocessed should the web fail to meet specifications.

The fibers used in the examples which follow were prepared as described in U.S. Pat. No. 4,148,664. The fibers consisted of a water-insoluble, ionizable partial hydrogen chloride salt of collagen containing about 84% of the theoretical stoichiometric bound acid content. The bulk density of the mass of fibers was 2.0–2.5 lbs./cu.ft. (0.032–0.040 g./cc.). The fiber mass was processed in a conventional Rando-feeder. The fibers are converted into a bulky feed mat which is doffed from the feed mat condenser screen as it enters the Rando-webber. The mat passes over a feed plate and under a feed roll which pushes the mat into the nose bar and into the path of the rotating lickerin drum. The lickerin drum combs the fiber bundles from the feed mat and introduces the fiber bundles into an air stream. The fibers are carried by the air stream in a closed system to a revolving condenser screen on which the fibers are deposited uniformly over the screen to form a continuous, randomized, high bulk (low density) fiber mat. As the mat emerges from the condenser screen and is delivered to a moving conveyor it passes under a 5 pound rotating roll to lightly condense or compress the mat so as to provide the mat with sufficient coherence for subsequent calendering. The lightly compressed web as it leaves the conveyor is sandwiched between two moving glassine sheets.

Under normal operating conditions, the web as it leaves the Rando-webber will contain between about 7% and about 15% moisture, the moisture content of the original mass of fibers. As indicated, the moisture content of the web when calendered should be within the range of from about 5% to about 15%. When calendering by the use of embossing or pattern rolls, the moisture content is preferably between about 5% and about 12%, whereas, when calendering by the use of plain rolls, the moisture content is preferably between about 7% and about 12%. Where the moisture content of the web as it leaves the Rando-webber and is condensed by the rotating roll is not at a desired value for the specific calendering operation, the moisture content may be adjusted by passing hot, dry air or hot, humid air through the condensed web to either decrease or increase the moisture content, as desired, prior to interposing the web between the two glassine sheets.

In view of the fact that the Rando-feeder and Rando-webber (Rando Corporation, Macedon, N.Y. 14502) constitute conventional commercial equipment used in the production of dry, air-laid fibrous webs, no further detailed description of this equipment is deemed necessary.

Because of the weakness of the web as it leaves the Rando-webber, it is essential to support the continuous web while being transported to the calender rolls. In the production of the web for medical purposes, the cover sheet protects the web from possible extraneous foreign particles. The glassine sheets carry the interposed web through the calendering rolls and thence to a reel upon which the sheets and interposed web are collected. In calendering the mat, the calender rolls effect a 40 to 60% reduction in thickness. The calendering operation is required so as to impart sufficient integrity to the web so that it may withstand cutting, handling, packaging and finally application to a wound. The calendering under the conditions mentioned will result in the retention of the hemostatic, adhesive and delamination modes of action of the web. In the calendering operation the moisture acts as both a plasticizer and a bonding agent for the fibers.

The examples which follow are illustrative of the practice of the present method. In general, the basis weight of the webs produced for the present purposes will be within the range of about 200 to about 400 gm. per sq. meter, preferably within a range of about 220 to 350 gms. per sq. meter and an initial thickness of between about 2 to about 4 mm. The calendered thickness will generally be within the range of about 1.0 to 2.0 mm., preferably about 1.2 to 1.5 mm. In all instances, the Rando-feeder and Rando-webber were operated in a room wherein the ambient atmosphere was maintained at about 24° C. and an RH of about 50%.

RUNS A, B AND C

A mass of fibers was delivered by the Rando-feeder at a rate so as to produce webs having basis weights between about 300 and 350 gms. per sq. meter. The operating conditions of the Rando-feeder and the Rando-webber for representative operation of the equipment are set forth in Table I. As the web left the final conveyor of the Rando-webber it was sandwiched between two glassine sheets (1.25 mil, 31.75μ, thickness) and thence passed to smooth-surfaced calender rolls spaced apart 0.64 mm. From the rolls, the glassine sheets and interposed web were collected on a reel. The resiliency or springiness of the webs, due in part to the loose bonding between fibers, is apparent from these data. Although the webs were passed through a 0.64 mm. gap between the calender rolls, upon release of the pressure, the webs expanded to a thickness of roughly twice the roll spacing. The web as delivered by the Rando-webber condenser screen is of exceedingly low density at these basis weights and can not be handled manually because of its very low strength. Accordingly, as described above, as the web leaves the take away conveyor it is pressed by a 5 pound roll to provide sufficient coherence to allow calendering. It is essential that the web be calendered so as to provide sufficient strength, coherence and rigidity to allow cutting and handling.

Calendering of the web is an essential step in the production of a satisfactory web. This operation involves critical factors in order to retain the hemostatic efficacy of the web and yet improve the coherence and integrity of the web to permit manual handling. It has been found that the moisture content during calendering is the most critical factor. In general, the lower the moisture content, the less sensitive the calendering operation. While calendering by the use of smooth-surfaced rolls, as shown by Runs A, B and C, is completely satisfactory, the use of pattern or embossing rolls allows a wider range of calendering conditions while simultaneously improving the integrity and stiffness or rigidity of the web.

RUNS D-J

Additional webs having basis weights between about 200 and 350 gms. per sq. meter were prepared. Samples of these webs of differing moisture contents and interposed between glassine sheets were calendered by pressing between two 6 in.×6 in. (15.25 cm.×15.25 cm.) plates in a manually operated, laboratory hydraulic press at pressures of 500 to 800 psi. (35.15 to 56.25 kg. per sq. cm.) and holding the pressure for 2 minutes. In the case of the plain or smooth-surfaced plates, shims having a thickness of 0.64 mm. were secured to the face of one of the plates at its four corners. In the case of the pattern plates (wave pattern), shims of a thickness corresponding to the depth of the wave were secured to the mating faces of each of the plates at their four corners. The wave pattern plates, male and female, were provided with longitudinally extending waves in the form of a sine wave, each wave having a width of 3 cm. and a pitch of 4.4 cm., the waves being spaced apart 3 cm. The effective calendering area for both plain and pattern plates was 5 in.×5 in. (12.7 cm.×12.7 cm.).

Following calendering, samples of the webs were dried by heating in an air circulating oven at 110° C. for 2 hours prior to determining their physical properties as shown in Table II. Other samples were dried at 110° C. for 2 hours and then sterilized by heating to about 126° C. for 20 hours followed by evaluating the samples by an "in vivo" surgical procedure. The evaluation of the samples is shown in Table II.

The "in vivo" surgical procedures were carried out on anaesthetized mongrel dogs. The spleen of the dog was exposed and excised wounds were made, the wounds measured about 20 mm.×10 mm. with a depth of about 1 to 2 mm. Swatches were cut from sample webs prepared as described above, the swatches being about 28 to 30 mm.×18×20 mm. so as to overlap the wound 4 to 5 mm. on all sides. The investigators were provided with the sample webs without a knowledge of the history of the samples so that all evaluation was "blind."

A wound was swabbed with a dry, surgical cotton gauze pad so as to provide a freely bleeding wound and a swatch immediately placed over the wound. The swatch was held in place by the application of pressure for 60 seconds and the pad lifted to determine whether hemostasis had been effected.

Delamination was determined after the swatch had been on the wound for 20 to 25 minutes. In this determination, excess material was removed by grasping the overlapping edges of the swatch with forceps and lifting the free edges. The adhesion of the material to the wound surface and the ease of the removal of the material in excess of that required to prevent rebleeding of the wound was noted. The handling characteristics included a consideration of the physical properties of the webs such as cohesiveness and flakiness of the webs, the friability, the stiffness and ability of the web to conform to the wound surface and the ability to cut swatches of a required size from the sheet with scissors to form clean cut edges.

In the evaluation of the webs in the "in vivo" procedures, the primary consideration is the hemostatic and adhesive interaction on the wound. Where these characteristics are "satisfactory", the product is acceptable so long as the "handling" and delamination properties are considered at least "good."

It will be noted from these evaluations that the webs produced in Runs D-G and I were acceptable. The web produced in Run H was unsatisfactory as a hemostat. This unsatisfactory nature was due to a deeper embossing depth at the higher moisture level as compared to the web of Run F at a moisture level of 8.8%. At the lesser embossing depths, Runs E and J, the web of Run E was acceptable as compared to the web of Run J. The latter web was unsatisfactory from a hemostat consideration because it was embossed at a moisture content close to the upper limit of moisture content. The web of Run I also calendered using plain plates at the high moisture content was satisfactory.

RUNS K-N

Additional experimental calendering was performed on webs of a basis weight of about 250 gms. per sq. meter and at high moisture contents. In all instances the webs were interposed between two glassine sheets. In Run K, calendering was effected by a 3×3 mm. basket weave roll (Roehlen Engraving Co., Rochester, N.Y., No. 69 RE 77), the pattern having a depth of 0.50 mm. operating against a smooth surfaced roll. Runs L and M utilized the previous described wave pattern plates $W_2$—0.75 mm. depth and $W_1$—0.50 mm. depth, respectively. Run N utilized the previously described smooth plates. The characteristics and evaluation of the webs of these runs are presented in Table III.

Two different investigators reported that all samples were acceptable and both expressed a preference for the web of Run M for general overall characteristics. Both investigators also indicated that in their individual opinions the web of Run L was slightly stiff and too compressed from the handling standpoint. The report that this web was somewhat stiff was probably predictable because of the depth of the calendering pattern coupled with the high moisture content, although the web was acceptable. One investigator stated that the web of Run K was more aesthetically appealing but was slightly more friable than the web of Run M. The investigators reported that in their opinions the web of Run K was not as good as the webs of Runs L and M and allowed slight bleed-through at points. Such action in the "in vivo" testing was due to variations in thickness of the web particularly at the junctions in the basket weave pattern. The web of Run N was said to be somewhat friable. The term "friable" is used in the sense that upon drawing a finger over the web, fibers become loosened from the surface of a mat.

As is apparent from the data in the foregoing tables, the webs of the present method are of very low basis weights as compared to ordinary writing papers. When calendering the webs by the use of smooth-surfaced rolls at ordinary ambient temperatures, slight variations in web density over the area of the web may create some buckling in the web. Buckling may affect adversely intimate contact with a wound surface. Also, such calendering results in web growth in both the machine and transverse directions. Furthermore, the web may be friable and of poor strength from the standpoint of mechanized cutting the web into desired dosage sized pieces. Where these disadvantages are encountered, they may be partially overcome by the use of embossing rolls. Suitable embossing rolls may correspond to the wave pattern plates, $W_1$ the wave having a depth of 0.50 mm. Such calendering does not completely eliminate buckling, however, because of the pattern imparted by the rolls the buckling is not noticeable. The web growth in the machine direction is reduced although the growth in the transverse direction is not affected. This type of calendering improves the strength and rigidity of the web allowing ready cutting in a mechanized cutting machine into dosage pieces. The specific data on the calendering at room temperature in a two roll calender is shown in Table IV. In the reduction of the thickness of the web from 3-3.5 mm. by a single pass between two rolls spaced apart 1.25 mm. some buckling of the web may occur.

Buckling in the calendered web and web growth due to calendering may be eliminated by calendering with heated rolls. As shown by the data in Table IV, maintaining the calender rolls at a temperature of 95°-96° C. eliminates buckling and results in a slight shrinkage of the web in both machine and transverse directions. The calendered web is coherent and of sufficient strength and rigidity so that the glassine sheets may be removed and the web pushed over the table of a mechanized cutting machine. The cutting machine severs the web longitudinally into strips of a desired size and the strips cut transversely into desired dosage sizes.

Buckling of the web, when encountered, may be overcome by the use of a 3-roll calender at room and elevated temperatures, as shown by the data in Table V.

In such calendering, the spacing between the first and second rolls is preferably greater than the spacing between the second and third rolls although the spacings may be identical. Although such calendering overcomes buckling, when conducted at room temperatures, web growth results and the web is of low strength and rigidity from the standpoint of mechanized cutting. The data illustrate that by maintaining the calender rolls at a temperature of 95°-96° C. buckling of the web is overcome and the web will exhibit a slight shrinkage in both directions. The strength and rigidity of the web is increased sufficiently so as to allow mechanized cutting.

Buckling may be eliminated and the improvement in strength and rigidity may be obtained with substantially no observable growth and no observable shrinkage of the web by maintaining the calender rolls, in both a 2-roll and 3-roll calender, at temperatures between about 65° and about 75° C. In general, when calendering with heated rolls, the webs may have a moisture content in the lower portion of the ranges discussed hereinbefore with the retention of the desired properties in the webs. For plain roll calendering, the web preferably contains between about 7 and 12% moisture. For pattern or embossing roll calendering, the web preferably contains between about 5 and 12% moisture. As apparent from the foregoing discussion and the data in the tables, calendering with both 2-roll and 3-roll calenders, either plain or pattern rolls, may be effected at temperatures from ambient room temperature to about 95° C., preferably between 65° and 75° C.

The foregoing discussion and the in vivo evaluations illustrate that severed biological surfaces may be joined and a wound sealed without the use of sutures by the application of the webs of this invention. Severed biological surfaces as discussed herein include cut, sliced, ripped, torn, abraded, punctured, burned and tissue severed by any means or method whereby a fresh biological surface is present. Biological surfaces include tissue, cartilage, vessels, bone and other normal organic parts of the warm blooded animal which may require mending or joining. The terms "adhesion" and "adhesive" as used in this specification are used in the mechanical and chemical sense to designate what might be termed a cementing or gluing action and do not have reference to the normal medical designations.

TABLE I

| | Rando Machine Operating Conditions | | | Web Properties | | | |
|---|---|---|---|---|---|---|---|
| Run | Feeder Condenser Screen Speed-m/min. | Auxiliary Roll to Feed Plate Gap - mm. | Feed Roll to Nose Bar Gap - mm. | Moisture % | Initial thickness mm. | Calendered thickness mm.* | Basis weight gms/sq. m. |
| A | 0.61 | 7.1 | 2.2 | 9.9 | 3.5 | 1.3 | 317 |
| B | 0.46 | 5.6 | 5.3 | 10.9 | 3.4 | 1.2 | 308 |
| C | 0.61 | 7.1 | 2.2 | 10.9 | 3.6 | 1.4 | 340 |

*All calendered with 2 plain rolls - 0.64 mm. gap between rolls

TABLE II

| | Web Physical Properties | | | | | | In vivo Evaluation | | | |
|---|---|---|---|---|---|---|---|---|---|---|
| Run | H₂O % | Basis Wt. gm./sq. m. | Plate Type | Thickness mm. | Disintegration sec. | Wettability sec. | Water holding capacity gms./gm. | Hemostat | Adhesion | Handling | Delamination |
| D | 8.8 | 220 | P | 1.32 | 7 | 6 | 18.8 | S | S | G | E |
| E | 8.8 | 365 | $W_1$ | 1.62 | 11 | 7 | 20.4 | S | S | G | E |
| F | 8.8 | 230 | $W_2$ | 1.00 | 9 | 6 | 18.9 | S | S | G | G |
| G | 11.6 | 344 | P | 1.57 | 6 | 5 | 19.4 | S | S | G | E |
| H | 12.3 | 278 | $W_2$ | 1.03 | no | 4 | 17.6 | U | S | F | P |
| I | 14.7 | 314 | P | 1.43 | 9 | 7 | 19.5 | S | S | G | G |

TABLE II-continued

| | | Web Physical Properties | | | | | In vivo Evaluation | | | |
|---|---|---|---|---|---|---|---|---|---|---|
| Run | H₂O % | Basis Wt. gm./sq. m. | Plate Type | Thickness mm. | Disintegration sec. | Wettability sec. | Water holding capacity gms./gm. | Hemostat | Adhesion | Handling | Delamination |
| J | 14.7 | 250 | $W_1$ | 1.01 | 8 | 4 | 21.6 | U | S | G | E |

P - Plain plates
$W_1$ - Wave pattern, 0.5 mm. depth
$W_2$ - Wave pattern, 0.75 mm. depth
S - Satisfactory
G - Good
E - Excellent
F - Fair
P - Poor
U - Unsatisfactory

TABLE III

| Run | Calender Type of Pattern | Web Properties Moisture % | Thickness mm. | In vivo Evaluation Hemostat/Adhesive | Delamination | Handling |
|---|---|---|---|---|---|---|
| K | 3 × 3 mm. Basket Weave 1 side " 1 side plain | 13.4 | 1.25 | S | S | Slightly friable |
| L | Wave Pattern $W_2$ - See Runs F & H | 14.7 | 1.19 | S | S | Slightly stiff |
| M | Wave Pattern $W_1$ - See Runs E & J | 14.7 | 1.11 | S | S | Good |
| N | Plain | 14.7 | 1.26 | S | S | Friable |

S - Satisfactory

TABLE IV

| Calender rolls | 2 | 2 | 2 |
|---|---|---|---|
| Roll spacing, mm. | 1.25 | 1.25 | 1.25 |
| Type of roll | Plain | Wave | Plain |
| Roll temp, °C. | 24 | 24 | 95–96 |
| Web thickness, mm., initial | 3–3.5 | 3–3.5 | 3–3.5 |
| Web moisture, % | 12 | 12 | 12 |
| Web growth | | | |
| Machine direction | +3% | +1% | −1% |
| Transverse direct. | +2% | +2% | −1% |
| Web properties | | | |
| Buckling | Yes | Not Apparent | None |
| Strength | Friable | Coherent | Coherent |
| Machine cutting | No | Yes | Yes |
| Thickness, mm., final | 1.3–1.4 | 1.3–1.4 | 1.3–1.4 |

TABLE V

| Calender rolls | 3 | 3 |
|---|---|---|
| Roll spacing | | |
| ¼, mm. | 1.95 | 1.95 |
| ⅜, mm. | 1.2 | 1.2 |
| Type of rolls | Plain | Plain |
| Roll temperature, °C. | 24 | 95–96 |
| Web thickness, mm., initial | 3–3.5 | 3–3.5 |
| Web moisture, % | 12 | 12 |
| Web growth | | |
| Machine direction | +4% | −2% |
| Transverse direction | +3% | −1% |
| Web properties | | |
| Buckling | None | None |
| Strength | Weak | Coherent |
| Machine cutting | No | Yes |
| Thickness, mm., final | 1.35 | 1.35 |

What is claimed is:

1. A hemostatic-adhesive, collagen dressing for severed biological surfaces, comprising a dry-laid, nonwoven, self-supporting web formed from a mass of hemostatic-adhesive, collagen fibers having a moisture content of from about 7% to about 15% by weight, said collagen fibers consisting essentially of an ionizable, water insoluble, partial acid salt of collagen containing from about 50% to about 90% of the theoretical stoichiometric amount of ionizable acid, said web having been calendered to improve its integrity.

2. A hemostatic-adhesive, collagen dressing according to claim 1, wherein the hemostatic-adhesive properties of the mass of collagen fibers are retained by the web.

3. A hemostatic-adhesive, collagen dressing according to claim 1, wherein the partial acid salt of collagen consists essentially of an ionizable, water insoluble, partial acid salt of collagen containing from about 60% to about 85% of the theoretical stoichiometric amount of ionizable acid.

4. A hemostatic-adhesive, collagen dressing according to claim 1, wherein the partial acid salt of collagen consists essentially of a partial hydrogen chloride salt of collagen.

5. A hemostatic-adhesive, collagen dressing according to claim 3, wherein the partial acid salt of collagen consists essentially of a partial hydrogen chloride salt of collagen.

6. A hemostatic-adhesive, collagen dressing according to claim 1, wherein the partial acid salt of collagen consists essentially of a partial hydrogen chloride salt of collagen containing about 84% of the theoretical stoichiometric amount of hydrogen chloride.

7. A hemostatic-adhesive, collagen dressing according to claim 1, wherein the web has a basis weight of from about 200 to about 400 grams per square meter and a thickness of about 1 to 2 millimeters.

8. A method of preparing a hemostatic-adhesive, collagen dressing for severed biological surfaces in the form of a dry-laid, non-woven, self-supporting web of collagen fibers which comprises supplying a mass of hemostatic-adhesive, collagen fibers having a moisture content of from about 7% to about 15% by weight to conventional air-laying web forming equipment to convert the mass of fibers into a dry-laid, non-woven web, said collagen fibers consisting essentially of an ionizable, water insoluble, partial acid salt of collagen containing from about 50% to about 90% of the theoretical stoichiometric amount of ionizable acid, and calendering the web to provide a self-supporting web structure.

9. A method of forming a dry-laid, non-woven web of collagen fibers according to claim 8, wherein the hemostatic-adhesive properties of the mass of collagen fibers are retained by the web.

10. A method of preparing a dry-laid, non-woven, self-supporting web of collagen fibers according to claim 8, wherein the partial acid salt of collagen consists essentially of an ionizable, water insoluble, partial acid salt of collagen containing from about 60% to about 85% of the theoretical stoichiometric amount of ionizable acid.

11. A method of preparing a dry-laid, non-woven, self-supporting web of collagen fibers according to claim 8, wherein the partial acid salt of collagen consists essentially of a partial hydrogen chloride salt of collagen.

12. A method of preparing a dry-laid, non-woven, self-supporting web of collagen fibers according to claim 8, wherein the web has a moisture content of from about 5% to about 15% by weight when calendered.

13. A method of preparing a dry-laid, non-woven, self-supporting web of collagen fibers according to claim 8, wherein the web has a moisture content of from about 7% to about 12% by weight when calendered and is calendered by the use of plain rolls.

14. A method of preparing a dry-laid, non-woven, self-supporting web of collagen fibers according to claim 8, wherein the web has a moisture content of from about 5% to about 12% by weight when calendered and is calendered by the use of embossing rolls.

15. A method of preparing a dry-laid, non-woven, self-supporting web of collagen fibers according to claim 8, wherein the air circulating in the air-laying web forming equipment and the ambient atmosphere surrounding that equipment are maintained at a temperature of 21° to 24° C. and a relative humidity of 50 to 55% when the mass of hemostatic-adhesive collagen fibers is supplied thereto.

16. A hemostatic-adhesive, collagen dressing for severed biological surfaces, comprising a dry-laid, non-woven, self-supporting web formed from a mass of hemostatic-adhesive, collagen fibers having a moisture content of 8% to 11% by weight, said collagen fibers consisting essentially of an ionizable, water insoluble, partial acid salt of collagen containing from about 60% to 85% of the theoretical stoichiometric amount of ionizable acid, said web having been calendered to improve its integrity.

17. A hemostatic-adhesive, collagen dressing according to claim 16, wherein the partial acid salt of collagen consists essentially of a partial hydrogen chloride salt of collagen.

18. A hemostatic-adhesive, collagen dressing according to claim 16, wherein the partial acid salt of collagen consists essentially of a partial hydrogen chloride salt of collagen containing about 84% of the theoretical stoichiometric amount of hydrogen chloride.

19. A hemostatic-adhesive, collagen dressing according to claim 16, wherein the web has basis weight of from about 200 to about 400 grams per square meter and a thickness of about 1 to 2 millimeters.

* * * * *